United States Patent
Dolitzky et al.

(10) Patent No.: US 7,038,060 B2
(45) Date of Patent: May 2, 2006

(54) SYNTHESIS OF 2-BUTYL-3-(2'-(1-TRITYL-1H-TETRAZOL-5-YL)BIPHENYL-4-YL)-1,3-DIAZASPIRO[4.4]-NON-ENE-4-ONE

(75) Inventors: Ben-Zion Dolitzky, Petach Tiqva (IL); Julia Kaftanov, Haifa (IL); Boris Pertsikov, Nesher (IL); Igor Rukhman, Haifa (IL); Gennady Nisnevich, Haifa (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 65 days.

(21) Appl. No.: 10/773,414

(22) Filed: Feb. 5, 2004

(65) Prior Publication Data
US 2004/0242894 A1 Dec. 2, 2004

Related U.S. Application Data

(60) Provisional application No. 60/465,905, filed on Apr. 28, 2003, provisional application No. 60/445,218, filed on Feb. 5, 2003.

(51) Int. Cl.
 *C07D 257/04* (2006.01)
 *C07D 403/10* (2006.01)
 *C07D 487/10* (2006.01)
 *C07C 69/74* (2006.01)

(52) U.S. Cl. .................. 548/253; 548/250; 560/122

(58) Field of Classification Search ................ 548/253, 548/250; 560/122
See application file for complete search history.

(56) References Cited

U.S. PATENT DOCUMENTS

| | | | | |
|---|---|---|---|---|
| 5,270,317 A | * | 12/1993 | Bernhart et al. | 514/269 |
| 5,541,209 A | * | 7/1996 | Spinale | 514/381 |
| 5,559,233 A | * | 9/1996 | Bernhart et al. | 544/321 |
| 5,629,331 A | | 5/1997 | Caron et al. | |
| 6,800,761 B1 | * | 10/2004 | Franc et al. | 548/253 |
| 2004/0192713 A1 | * | 9/2004 | Nisnevich et al. | 514/278 |
| 2005/0032862 A1 | * | 2/2005 | Franc et al. | 514/381 |
| 2005/0176794 A1 | * | 8/2005 | Dolitzky et al. | 514/381 |

FOREIGN PATENT DOCUMENTS

WO WO 9906398 A1 * 2/1999
WO WO 2004/007482 A 1/2004

OTHER PUBLICATIONS

Le Bourdonnec, B., et al., "Synthesis and Pharmacological Evaluation of New Pyrazolidine-3,5-diones as AT1 Angiotensin II Receptor Antagonists," J. Med. Chem., vol. 43(14), pp. 2685-2697 (2000), at p. 2687, Scheme 2, "reaction b" with compound 19.*

* cited by examiner

*Primary Examiner*—Kamal A. Saeed
*Assistant Examiner*—Anthony J. Paviglianiti
(74) *Attorney, Agent, or Firm*—Kenyon & Kenyon

(57) ABSTRACT

Provided is a novel method of making 2-butyl-3-[[2'(1-trityl-1H-tetrazol-5-yl)biphen-4-yl]methyl]-1,3-diazaspiro[4.4]non-1-ene-4-one, which can be converted to irbesartan. Also provided are methods of making irbesartan.

11 Claims, No Drawings

US 7,038,060 B2

SYNTHESIS OF 2-BUTYL-3-(2'-(1-TRITYL-1H-TETRAZOL-5-YL)BIPHENYL-4-YL)-1,3-DIAZASPIRO[4.4]-NON-ENE-4-ONE

RELATED APPLICATIONS

The present invention claims the benefit of the filing dates of U.S. Provisional Patent Applications 60/445,218, filed Feb. 5, 2003, and 60/465,905, filed Apr. 28, 2003, the contents of which are incorporated herein.

FIELD OF THE INVENTION

The present invention relates to methods of making irbesartan and, especially, a precursor therefor.

BACKGROUND OF THE INVENTION

Irbesartan is a known angiotensin II receptor antagonist (blocker). Angiotensin is an important participant in the renin-angiotensin-aldosterone system (RAAS) and has a strong influence on blood pressure. Irbesartan has the chemical name 2-butyl-3-[[2'-(1H-tetrazole-5-yl)biphenyl-4-yl]methyl]-1,3-diazaspiro[4.4]non-1-en-4-one. The structure of irbesartan is shown below (I).

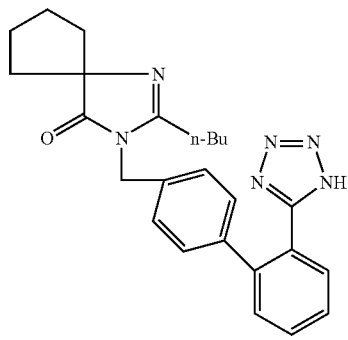

(I)

The synthesis of irbesartan is discussed, inter alia, in U.S. Pat. Nos. 5,270,317 and 5,559,233; both of which are incorporated herein in their entirety by reference. In the synthesis therein disclosed, the prepenultimate reaction step (exclusive of work-up and purification) involves the reaction of a cyano group on the biphenyl ring with an azide, for example tributyltin azide. Reaction times as long as 210 hours can be required. See, e.g., '317 patent.

U.S. Pat. No. 5,629,331 also discloses a synthesis of irbesartan from a precursor 2-n-butyl-3-[(2'-cyanobiphenyl-4-yl)methyl]-1,3-diazaspiro[4.4]non-1-ene-4-one with sodium azide using a dipolar aprotic solvent. As acknowledged in the '331 patent, there are safety risks involved in the use of azides (column 4, line 39). Also, dipolar aprotic solvents (e.g. methylpyrrolidone) are relatively high boiling and can be difficult to remove.

There is a need for an improved synthetic route to irbesartan, its derivatives and its precursors.

SUMMARY OF THE INVENTION

In one aspect, the present invention relates to a process of making a compound of

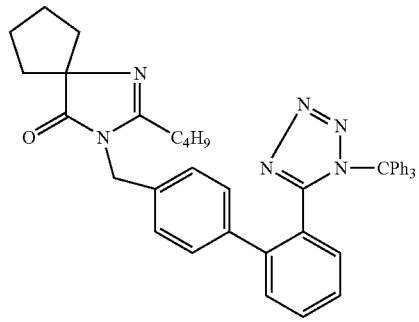

structure II including the steps of: reacting, especially at reflux, 1(N'-pentanoylamino)cyclopentanecarboxylic acid amide with 5-(4'-bromomethylbiphenyl-2-yl)-1-trityl-1H-tetrazole in the presence of an inorganic base, especially NaOH, KOH, or Na2CO3 (or a mixture of these); a solvent, especially an aliphatic ether having up to 8 carbon atoms or an aromatic hydrocarbon (especially dry toluene); and a phase transfer catalyst, especially tetrabutylammonium sulfate; cooling the mixture; adding water to the mixture whereby two phases are obtained; separating the two phases obtained; and recovering the compound of structure II.

In another embodiment, the present invention relates to a process of making a compound of structure II including the steps of: reacting, for a period of time of about 2 to about 24 hours, a valerimidate derivative, especially ethyl valerimidate or a salt thereof, with a first amine, especially 5'-(4'aminomethylbiphenyl-2-yl)-1-trityl-1H-tetrazole or 1-aminocyclopentane carboxylic acid ethyl ester, in the presence of a first acid, especially HCl, and an organic solvent, especially dry toluene, to form a mixture; cooling the mixture; combining the mixture with a second amine especially 5'-(4'aminomethylbiphenyl-2-yl)-1-trityl-1H-tetrazole or 1-aminocyclopentane carboxylic acid ethyl ester (with the proviso that first and second amines are not the same, and a catalytic amount of a second acid, especially acetic acid; heating the combination at reflux for about 2 to about 24 hours; contacting the combination with a base, especially a base in solution in water whereby two phases are obtained; separating the phases obtained; and recovering the compound of structure II.

In another aspect, the present invention relates to a method of making a compound of structure II including the steps of: combining a valeramide derivative, estecially ethyl valerimidate, with a base scavenger, especially 2,6-lutidine, and oxalyl chloride in the presence of an organic solvent, especially dry toluene; cooling the resulting combination; maintaining the combination for between 0.25 and 4 hours, whereby an inidoyl chloride intermediate is presumed to form; further combining an amine, especially 5'-(4'aminomethylbiphenyl-2-yl)-1-trityl-1H-tetrazole or 1-aminocyclopentane carboxylic acid ethyl ester, and an organic solvent with the combination; heating the resulting combination to reflux for about 0.1 to about 1 hours; thereafter contacting the mixture with a base, especially an aqueous solution of anninorganic base whereby two phases are obtained; separating the phases obtained; and recovering the compound of structure II.

In yet another aspect, the present invention relates to a method of making irbesartan including the step of converting, by removing the trityl group, 2-butyl-3-[[2'-(1-trityl-1H-tetrazol-5-yl)biphen-4-yl]methyl-1,3-diazaspiro[4.4]non-1-ene-4-one to irbesartan.

DETAILED DESCRIPTION OF THE INVENTION

The present invention provides a one-pot method of making 2-butyl-3-[2'-(1-trityl-1H-tetrazol-5-yl)biphenyl-4-ylmethyl]-1,3-diazaspiro[4.4]non-1-ene-4-one (Structure II, IRB-03, trityl irbesartan) from 1-pentanoylaminocyclopentanecarboxylic acid amide (N-pentanoyl-1-amino-1-carbamoylcyclopentane, IRB-23) and 5-(4'-bromomethylbiphenyl-2-yl)-1-trityl-1H-tetrazole (IRB-02) in an at least initially multi-phase system in the presence of a phase transfer catalyst. The multi-phase system can be biphasic (solid-liquid), or it can be triphasic (solid-liquid-liquid).

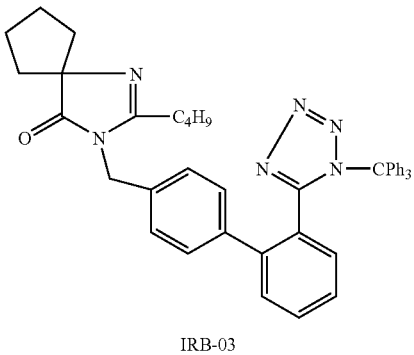

IRB-03

In biphasic embodiments of the present invention, IRB-23 is in suspension with an alkali metal hydroxide and an alkali metal carbonate in a first solvent in the presence of a phase transfer catalyst and the desired amount of IRB-02.

The preferred alkali metal carbonate is $K_2CO_3$. About 1.5 and preferably about 2 equivalents of alkali metal carbonate can be use for each equivalent of IRB-02. The preferred alkali metal hydroxide is NaOH. About 3 and preferably about 3.5 equivalents of alkali metyal hydroxide are used for each equivalent of IRB-02.

First solvents are organic compounds, liquid at about 20° C., that dissolve IRB-02, but that are substantially insoluble in water. A liquid organic compound is substantially insoluble in water if it is soluble in water to less than about 5% such that, if equal initial volumes of substantially insoluble organic liquid and water are mixed, a two-phase (liquid-liquid) system results, the total volume of which is approximately equal to the initial volume of water plus the initial volume of the substantially insoluble organic liquid.

First solvents useful in the practice of the present invention include linear and cyclic aliphatic ethers having up to 8 carbon atoms, for example methyl t-butyl ether and tetrahydrofuran, and aromatic hydrocarbons, for example toluene. The amount of frist solvent is not critical as long as sufficient first solvent is used so that the IRB-02 is in solution. Preferably, between about 3 and about 4 liters of first solvent are used per combined moles of IRB-02 and IRB-23.

Phase transfer catalysts are well known to one skilled in the art of organic synthesis. Phase transfer catalysts are of particular utility when at least first and second compounds to be reacted with each other have such different solubility characteristics that there is no practical common solvent for them and, accordingly, combining a solvent for one of them with a solvent for the other of them results in a two-phase system.

Typically, when such compounds are to be reacted, the first reactant is dissolved in a first solvent and the second reactant is dissolved in a second solvent. Because the solvent for the first reactant is essentially insoluble in the solvent for the second reactant, a two-phase system is formed and reaction occurs at the interface between the two phases. The rate of such an interfacial reaction can be greatly increased by use of a phase transfer catalyst (PTC).

Several classes of compounds are known to be capable of acting as phase transfer catalysts, for example quaternary ammonium compounds and phosphonium compounds, to mention just two. Tetrabutylammonium hydrogensulfate is a preferred PTC for use in the practice of present invention. Approximately 0.1 equivalents of phase tyransfer catalyst per equivalent of IRB-23 to be reacted is usually sufficient, but more or less can be used.

IRB-23 can be obtained by Schotten-Baumann reaction between 1-amino-1-carbamoylcyclopentane and valeroyl chloride in THF solvent using triethylamine as acid scavanger.

In biphasic embodiments, IRB-02, IRB-23, alkali metal carbonate, alkali metal hydroxide, phase transfer catalyst, and first solvent are combined, in any order, and heated, preferably to a temperature between about 80° C. and reflux, most preferably to a temperature of about 90° C. The reaction is allowed to proceed until substantially all of the IRB-02 has been consumed. The progress of the reaction can be monitored by, for example, thin layer chromatography (TLC) using hexane/ethyl acetate (1:1) eluent.

When substantially all of the IRB-02 has been consumed, the reaction mixture is cooled and diluted with water (ca. one to two times the volume of the reaction mixture). The first-solvent phase (organic phase) is separated and, optionally, washed with brine. Preferably, the water content of the first-solvent phase is reduced by, for example, treating it with a solid drying agent.

The desired product, IRB-03, can be isolated by concentrating the first-solvent phase to a residue and separating IRB-03 therefrom by column chromatography on a silica gel column using, for example, hexane/ethyl acetate (4:1 to 1:1) eluent. The composition of chromatography fractions can be determined by, for example, nuclear magnetic resonance spectroscopy. IRB-03 can be isolated from IRB-03-containing fractions by separating the eluent by, for example, distillation.

Triphasic embodiments of the present invention are analogous to the biphasic embodiments and include a second solvent that is essentially water, whereby at least a portion of the alkali metal carbonate, if any, and the alkali metal hydroxide are in solution in the second solvent. In these embodiments, the alkali metal carbonate is optional.

Thus, in triphasic embodiments, IRB-03, IRB-23, alkali metal hydroxide, optionally alkali metal carbonate, phase transfer catalyst, and first solvent are combined with second solvent. The amounts of reactants used in triphasic embodiments are essentially the same as in biphasic embodiments, however an excess, up to about a 100% excess, of IRB-23 is preferred. The volume of second solvent is about one-quarter to one-half of the volume of first solvent.

Work-up of the reaction mixture is analogous to that in biphasic embodiments. The first-solvent phase is separated and combined with first-solvent phase obtained by optional extracting of the second-solvent phase with first solvent. The first-solvent phases can the be treated, and the IRB-03 isolated, as in biphasic embodiments.

In another embodiment, the present invention provides a novel synthesis of irbesartan, analogues thereof, and, especially, precursors therefor (e.g. trityl irbesartan) including the step of reacting a reacting a valerimidate derivative with an amine to form an ester intermediate, and further reacting the ester intermediate with an amine to form 2-butyl-3-[[2'-(1-trityl-1H-tetrazole-5-yl)biphenyl-4-yl]methyl]-1,3-diazaspiro[4.4]non-1-en-4-one. The step is carried out in the presence of an acid. Preferably the step is carried out in the presence of one equivalent of acid per equivalent of valerimidate derivative. The valerimidate derivative can be any suitable derivative, including but not limited to ethers and esters. Preferred valerimidate derivatives include methyl, ethyl, propyl, butyl, benzyl, pentyl and aryl valerimidate esters (e.g. ester of valeroylimidic acid; $R_1$—C(=NH)—O—$R_2$; $R_1$=$C_4H_9$)), or, especially, salts thereof. A most preferred ester is the ethyl ester.

The reaction is carried out in an organic solvent. Examples of preferred organic solvents include, but are not limited to, N,N dimethyl formamide (DMF), dimethyl acetamide (DMA), toluene, hexane, 1,2-dimethoxyethane (DME), diethoxymethane, tetrahydrofuran (THF), benzene, m-xylene, o-xylene, tetralins, formals, glymes and mixtures thereof. A most preferred organic solvent is dry toluene. Other hydrocarbons useful in the practice of the present invention will be apparent to the skilled artisan.

The novel synthesis of irbesartan precursor, irbesartan itself, and analogues thereof, of the present invention includes the step of reacting a valerimidate derivative with an amine to form an N-substituted imido ester-like ester intermediate, and further reacting the ester intermediate with an amine to form 2-butyl-3-[[2'-(1-trityl-1H-tetrazole-5-yl)biphenyl-4-yl]methyl]-1,3-diazaspiro[4.4]non-1-en-4-one. Preferred amines include 5'-(4'aminomethylbiphenyl-2-yl)-1-trityl-1H-tetrazole (2-(1-trityl-1H-tetrazol-5-yl)-4'-aminomethylbiphenyl; Structure III; IRB-09) and 1-aminocyclopentane carboxylic acid ethyl ester (IRB-13).

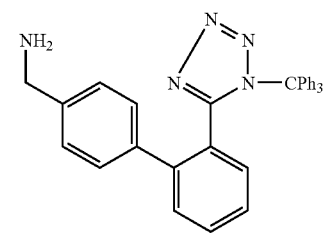

III

IRB-09

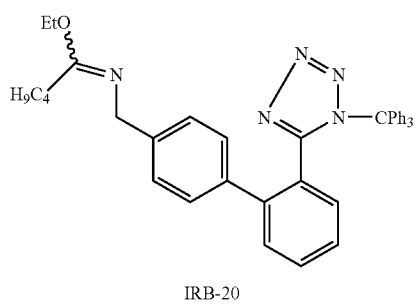

IV

IRB-20

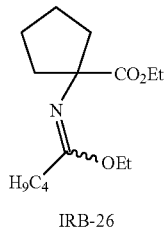

V

IRB-26

A preferred valerimidate derivative is ethyl valerimidate as its methanesulfonic acid salt. When the amine is IRB-09, the intermediate has structure IV (2-(1-trityl-1H-tetrazol-5-yl)-4'-(1''-ethoxypentanaminyl)biphenyl). When the amine is ethyl 1-amino-1-cyclopentanecarboxyalte, the intermediate has structure V.

The step is carried out in an organic solvent reaction system. To the organic solvent is added an amount of valerimidate derivative and an amount of an acidic material. The acidic material may be any suitable acid, including mineral acids, hydrogen sulfate, trifluoroacetic acid, formic acid, hydrobromic acid, acetic acid and formic acid. A most preferred acid is hydrochloric acid. The ratio of valerimidate derivative to acidic material can be from about 5:1 to about 1:0.5, the most preferred ratio is about 1:1. The resulting mixture is agitated at room temperature for a period of from about 6 to about 24 hours. Preferably the reaction mixture is agitated for a period of about 12 hours. The time of the reaction can be conveniently monitored using thin layer chromatography. Following completion of the reaction, the reaction mixture is cooled and precipitated by-products removed. Preferably the reaction mixture is cooled to a temperature of from about −15° C. to about 15° C. Most preferably the reaction mixture is cooled to a temperature of about 0° C. To the reaction mixture is added an amount of a suitable amine such as IRB-09 and RB-13, and a catalytic amount of an acid material added. Preferred acid materials include mineral acids, hydrogen sulfate, trifluoroacetic acid, formic acid, hydrobromic acid, acetic acid and formic acid. A most preferred acid is acetic acid. The reaction mixture is heated under reflux for a period of from 2 hours to about 10 hours. Preferably the reaction mixture is agitated for a period of from about 3 hours to about 5 hours. The time of the reaction can be conveniently monitored using thin layer chromatography. Following completion of the reaction, the reaction mixture is contacted with a base, preferably an inorganic base, more preferably a solution of an inorganic base in water, especially aqueous $NaHCO_3$, whereby essentially all of the acid in the reaction mixture is preferably neutralized. When aqueous base is used a two-phase (liquid-liquid) system results. If solid base is used, a two-phase (solid-liquid) system may result. In either instance, the resulting two-phase reaction system is separated. The organic phase is preferably washed and dried, and the reaction product, 2-butyl-3-[[2'-(1-trityl-1H-tetrazole-5-yl)biphenyl-4-yl]methyl]-1,3-diazaspiro[4.4]non-1-en-4-one, (IRB-03), separated out. The separation may be carried out by any known method, but is typically carried out by filtration and evaporation under reduced pressure.

Without wishing to be bound by theory, it is believed that the reaction proceeds via the production of imidate esters such as an N-valerimidate 5'-(4'aminomethylbiphenyl-2-yl)-1-trityl-1H-tetrazole (IRB-20) in the reaction of 5'-(4'aminomethylbiphenyl-2-yl)-1-trityl-1H-tetrazole (IRB-09) and ethyl valerimidate methanesulfonic acid salt, or an N-valerimidate-1-aminocyclopentane carboxylic acid ethyl ester (IRB-26) in the reaction of 1-aminocyclopentane carboxylic acid ethyl ester (IRB-09) and ethyl valerimidate methanesulfonic acid salt.

In another aspect, the novel synthesis of irbesartan, and analogues thereof, of the present invention, includes the step of reacting an amide with a base scavenger, preferably 2,6-lutidine, and oxalyl chloride, followed by the addition of an amine to form 2-butyl-3-[[2'-(1-trityl-1H-tetrazole-5-yl) biphenyl-4-yl]methyl]-1,3-diazaspiro[4.4]non-1-en-4-one.

The novel synthesis of irbesartan, and analogues thereof, of the present invention, includes the step of reacting a valerimidate derivative with 2,6-lutidine and oxalyl chloride to form a reaction mixture, and further adding an amine to form 2-butyl-3-[[2'-(1-trityl-1-H-tetrazole-5-yl)biphenyl-4-yl]methyl]-1,3-diazaspiro[4.4]non-1-en-4-one (IRB-03). Preferred valerimidate derivatives include cyclopentyl valeramide (IRB-23) and 5-(4'methylvaleramide-biphenyl-2-yl)-1-trityl-1H-tetrazole (IRB-10). Preferred amines include 2'-(1-trityl-1H-terazol-5-yl)biphenyl-4-ylmethylamine (IRB-09) and 1-amino cyclopentane carboxylic acid ethyl ester (IRB-13). The step is carried out in an organic solvent reaction system. To the organic solvent is added an amount of valeramide derivative and an amount of 2,6-lutidine. The reaction mixture is cooled to a temperature of from about −15° C. to about 15° C., and oxalyl chloride added. Most preferably the reaction mixture is cooled to a temperature of about 0° C. The ratio of 2,6-lutidine to oxalyl chloride can be from about 10:1 to about 1:5, the most preferred ratio is about 2:1. The resulting mixture is agitated for a period of from about 0.25 to about 4 hours. Preferably the reaction mixture is agitated for a period of about 1 hour. To the reaction mixture is added a solution of a suitable amine such as IRB-09 and IRB-13 in a suitable organic solvent, and the reaction mixture agitated for a period of about 0.1 to about 1 hour at about 0° C., then agitated for a period of about 0.1 to about 1 hour at about room temperature. The time of the reaction can be conveniently monitored using thin layer chromatography. Following completion of the reaction, the reaction mixture is neutralized with a molar excess of base, preferably aqueous NaHCO₃, and the resulting two-phase reaction system is separated. The organic phase is washed and dried, and the reaction product, 2-butyl-3-[[2'-(1-trityl-1H-tetrazole-5-yl)biphenyl-4-yl]methyl]-1,3-diazaspiro [4.4]non-1-en-4-one, (IRB-03), separated out. The separation may be carried out by any known method, but is typically carried out by filtration and evaporation under reduced pressure.

Without wishing to be bound by theory, it is believed that the reaction proceeds via the production of imidoyl chloride intermediates.

To obtain irbesartan, the compound of structure II obtained by any embodiment of the present invention can be dissolved in a suitable solvent, for example acetone, and the solution combined with aqueous hydrochloric acid (2–4 equivalents wrt. trityl compound of structure II). The mixture so obtained is combined with a water solution of an inorganic base, for example KOH. Solvent is removed (e.g. evaporated) from the resulting mixture and the trityl alcohol that precipitates is filtered-off. The pH of the filtrate is adjusted to about 4, cooled, and the resulting precipitate of irbesartan collected.

Of course, irbesartan can be obtained from the trityl compound of structure II by any other means known in the art.

The present invention in certain of its embodiments is illustrated by the following non-limiting examples.

EXAMPLE 1

Preparation of Irbesartan-Trityl (IRB-03) via Imidate Esters a) Preparation from 4'-aminomethyl-2-(1-trityl-1H-tetrazol-5-yl)biphenylvia the intermediate IRB-20:

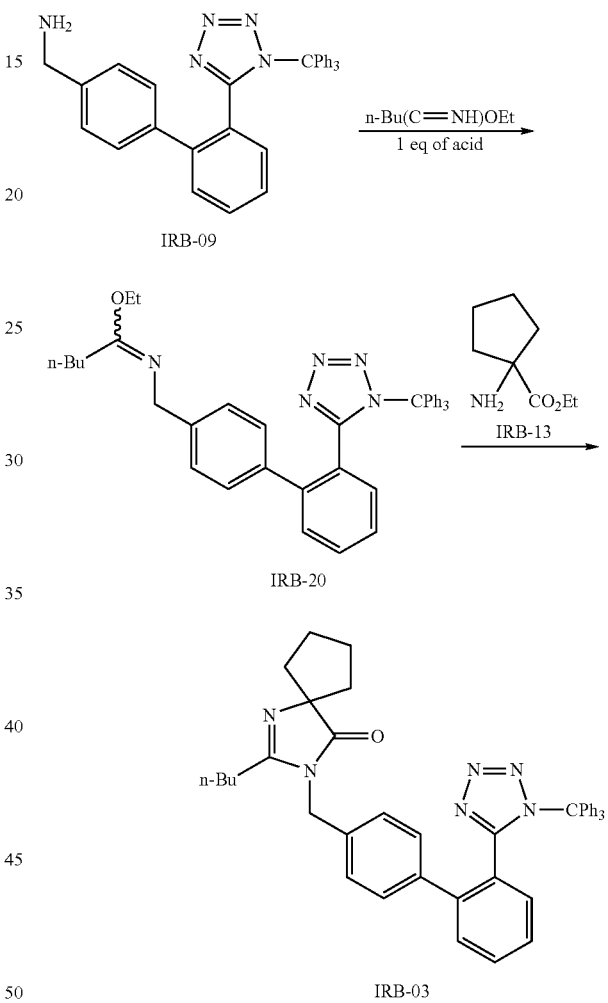

Ethyl 1-aminocyclopentane carboxylate (IRB-09; 2.2 g, 4.46 mmol) was mixed with ethyl valerimidate methanesulfonic acid salt (1.0 g, 4.45 mmol) in dry toluene (20 mL) under argon, and the reaction mixture was stirred for 12 hours at room temperature with TLC monitoring (hexane/ethyl acetate 2:1 and dichloromethane/methanol 10:1). The resulting suspension was cooled to 0° C. and precipitated ammonium methanesulfonate was filtered off. To the filtrate (25 mL) containing IRB-20 was added aminoester IRB-13 (0.7 g, 4.46 mmol) in one portion and the resulting mixture was stirred for 2 hours at room temperature. Acetic acid (catalytic amount, 4 drops) was added, and the reaction was refluxed for 5 hours with TLC monitoring (hexane/ethyl acetate 2:1). The reaction mixture was cooled to room temperature, washed with 10% aqueous NaHCO₃, water and brine, dried over Na₂SO₄, and filtered and evaporated under reduced pressure. The residue was chromatographed on a silica gel column to give 0.6 g (20% from IRB-09) of IRB-03 pure by NMR.

b) Preparation from 4'-aminomethyl-2-(1-trityl-1H-tetrazol-5-yl)biphenyl via the intermediate ethyl 1-(1'-ethoxy)pentanaminylcyclopentane carboxylate (IRB-26):

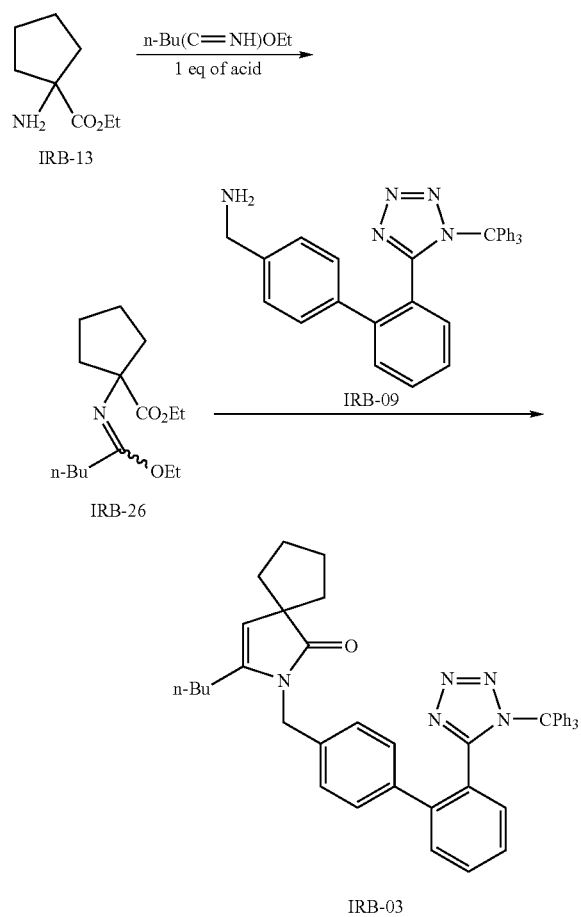

IRB-13 (0.7 g, 4.46 mmol) was mixed with ethyl valerimidate methanesulfonic acid salt (1.0 g, 4.45 mmol) in dry toluene under an inert atmosphere, and the reaction mixture was stirred for 24 hours at room temperature. The resulting suspension was cooled to 0° C. and the precipitated ammonium methanesulfonate was filtered off. To the filtrate (25 mL) containing IRB-26 was added amine IRB-09 (2.2 g, 4.46 mmol) in one portion followed by an addition of acetic acid (cat. amount, 4 drops). The reaction was refluxed for 3 hours with TLC monitoring (hexane/ethyl acetate 2:1), cooled to room temperature, washed with 10% aqueous NaHCO₃, water and brine, dried over Na₂SO₄, filtered and evaporated under reduced pressure. The residue was chromatographed on a silica gel column to give 1.5 g (50% from IRB-09) of IRB-03 pure by NMR.

EXAMPLE 2

Preparation of Irbesartan-Trityl (IRB-03) via Imidoyl Chlorides a) Preparation from starting material IRB-23:

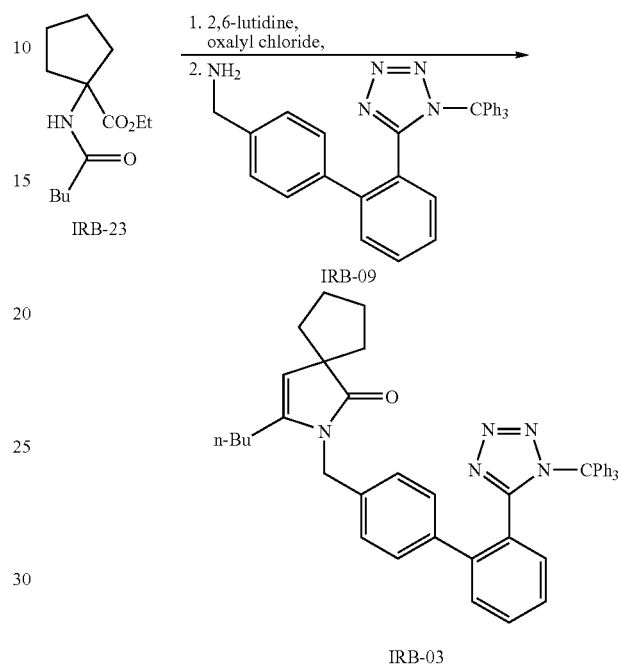

A solution of cyclopentyl valeramide, IRB-13 (1.0 g, 4.67 mmol) and 2,6-lutidine (1.25 g, 1.36 mL, 11.68 mmol) in dry toluene (10 mL) was cooled to 0° C. under argon, and oxalyl chloride (0.65 g, 0.45 mL, 5.14 mmol) was added dropwise. The resulting mixture was stirred for 1 hour at 0° C., and a solution of IRB-09 (2.31 g, 4.67 mmol) in dry toluene (25 mL) was slowly added. The reaction mixture was stirred for 30 minutes at 0° C., then for 30 minutes at room temperature, and then filtered. The filtrate was washed with 10% aqueous NaHCO₃, water and brine, dried over Na₂SO₄, filtered and evaporated under reduced pressure. HPLC detected about 40% of IRB-03 in the residue. Crystallization of the residue from isopropyl alcohol gave 0.94 g (about 30% from IRB-09) of IRB-03.

b) Preparation from starting material IRB-23:

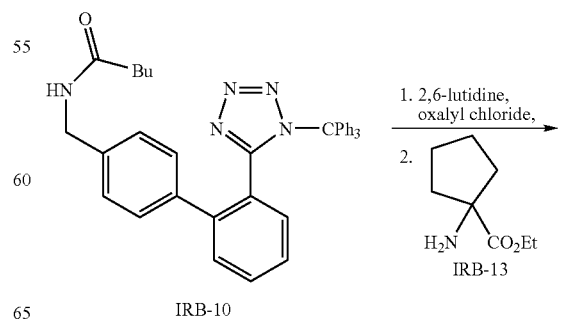

-continued

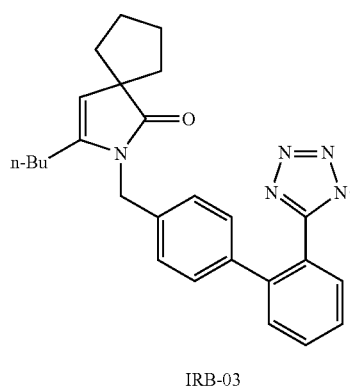

IRB-03

A solution of amide, IRB-10 (0.7 g, 1.21 mmol) and 2,6-lutidine (0.26 g, 0.28 mL, 2.42 mmol) in dry toluene (7 mL) was cooled to 0° C. under argon. Oxalyl chloride (0.17 g, 0.12 mL, 1.33 mmol) was added dropwise. The resulting mixture was stirred for 1 hour at 0° C., and IRB-13 (0.29 g, 1.21 mmol) in dry toluene (3 mL) was slowly added. The reaction was stirred for 30 minutes at 0° C., then for 30 minutes at room temperature, and then filtered. The filtrate was washed with 10% aqueous NaHCO$_3$, water and brine, dried over Na$_2$SO$_4$, filtered and evaporated under reduced pressure. HPLC detected about 30% of IRB-03 in the residue. The residue was chromatographed on a silica gel column to give 0.20 g (25% from IRB-10) of IRB-03 pure by NMR.

EXAMPLE 3

|  | Mw | grams, volume | mmol | Eq. |
| --- | --- | --- | --- | --- |
| IRB-23 | 212.1 | 3.0 g | 14.2 | 1.0 |
| IRB-02 | 557.5 | 7.9 g | 14.2 | 1.0 |
| NaOH | 40.1 | 2.0 g | 49.5 | 3.5 |
| K$_2$CO$_3$ | 138.1 | 3.9 g | 28.3 | 2.0 |
| Bu$_4$NHSO$_4$ | 339.54 | 0.48 g | 1.42 | 0.1 |
| Toluene | | Total 100 mL | | |
| 9.5 g | | | | |

A solution of IRB-02 in toluene (50 mL) was added dropwise, during 1 h, to the stirred suspension of IRB-23, finely powdered NaOH, K$_2$CO$_3$ and Bu$_4$NHSO$_4$ in toluene (50 mL) at 50° C. After the addition was completed, stirring was continued for 3 h at 90° C. (TLC monitoring: Hex/EtOAc 1:1, two points —IRB-03 and IRB-17). The resultant mixture was cooled to 50° C. Water (150 mL) was added and the resulting two-phase mixture was separated. The organic phase (first solvent) was washed with brine, dried over Na$_2$SO$_4$, filtered, and evaporated under reduced pressure. The semisolid residue was chromatographed on a short silica gel column (hexane/EtOAc 4:1 to 1:1) to give 5.0 g (53%) of IRB-03 and 3.0 g (32%) of IRB-17 that were pure by NMR.

EXAMPLE 4

|  | Mw | grams, volume | mmol | Eq. |
| --- | --- | --- | --- | --- |
| IRB-23 | 212.1 | 3.3 g | 15.6 | 1.5 |
| IRB-02 | 557.5 | 5.8 g | 10.4 | 1.0 |
| Potassium hydroxide, 85% | 56.11 | 1.85 g | 28.0 | 2.7 |
| Water | | 15 mL | | |
| Bu$_4$NHSO$_4$ | 339.54 | 0.53 g | 1.56 | 0.15 |
| Toluene | | 60 mL | | |
| 7.0 g/4.7 g | | | | |

A solution of IRB-02 in toluene was added to a stirred suspension of IRB-23 in a solution of KOH and Bu$_4$NHSO$_4$ in water at room temperature. After 20 min of stirring at room temperature no reaction was detected by TLC. The reaction was heated to 90° C. and stirred for 1.5 h until disappearance of IRB-02 (TLC monitoring; hexane/EtOAc 6:1). The mixture was cooled to room temperature, water (70 mL) was added and the phases were separated. The aqueous (second solvent) layer was extracted with toluene (30 mL) and the combined organics were washed with water (30 mL) and brine, dried over Na$_2$SO$_4$, filtered, and evaporated under reduced pressure to give 7.4 g of a semisolid residue (about 87% purity by HPLC). A portion of the residue (3.7 g) was crystallized from IPA to give 3.0 g (86% yield) of IRB-03 as a white powder (about 98% purity by HPLC). Another portion (3.7 g) of the residue was dissolved in acetone (30 mL) and 7.5 mL of aqueous 3N HCl (about 3 eq.) was added. After completion of deprotection (removal of trityly group, monitored by TLC) a solution of KOH (1.3 g) in 10 mL of water was slowly added and acetone was evaporated under reduced pressure. The precipitate (trityl alcohol) was filtered and washed with water (2×10 mL); the combined aqueous filtrate washed with 15 mL of EtOAc and slowly acidified to pH 4 with 3N aqueous HCl. The resulting suspension was cooled down to 0–4° C., stirred for additional 30 min and filtered. The filtercake was washed several times with water and dried under reduced pressure at 50–60° C., affording 2.0 g (about 85% yield from IRB-02) of IRB-00 (96% purity by HPLC).

EXAMPLE 5

|  | Mw | grams, volume | mmol | Eq. |
| --- | --- | --- | --- | --- |
| 1-Aminocyclopentane carboxylic acid amide | 128.2 | 12.8 g | 100 | 1.0 |
| Valeroyl Chloride | 120.6 | 13.3 g, 13.0 mL | 110 | 1.1 |
| Triethyl amine | 101.2 | 13.2 g, 18.1 mL | 130 | 1.3 |
| THF | | Total 100 mL | | |
| 21.2 g | | | | |

1-Aminocyclopentane carboxylic acid amide was suspended in a mixture of dry THF (80 mL) and Et$_3$N and cooled to 10° C. A Solution of valeroyl chloride in THF (20 mL) was slowly added with vigorous (preferably mechanical) stirring. The reaction temperature was kept below 30° C. and the resulted suspension was vigorously stirred for 1 h at room temperature (TLC monitoring: CH$_2$Cl$_2$/MeOH 8:1).

The solvent was evaporated under reduced pressure and the white residue was suspended in water (200 mL) and stirred for 20 min at room temperature. The solid was filtered, washed two times with water (total 100 mL) and methyl t-butyl ether (30 mL) and dried at 50° C./10 mmHg until constant weight to give 18.5 g (87.3% yield) of IRB-23 as a white powder pure by NMR. This product was used without additional purification.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

We claim:

1. A process of making a compound of structure I

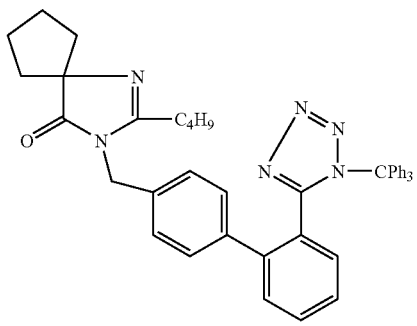

comprising the steps of:
 a) reacting 1(N'-pentanoylamino)cyclopentanecarboxylic acid amide with 5-(4'-bromomethylbiphenyl-2-yl)-1-trityl-1H-tetrazole in the presence of an inorganic base, a solvent and a phase transfer catalyst;
 b) cooling the mixture;
 c) adding water to the mixture whereby two phases are obtained;
 d) separating the two phases obtained; and
 e) recovering the compound of structure I.

2. The process of claim 1, wherein the inorganic base is selected from the group consisting of alkali metal hydroxides, alkali metal carbonates or mixtures thereof.

3. The process of claim 2, wherein the alkali metal hydroxides are NaOH or KOH, and the alkali metal carbonate is $K_2CO_3$.

4. The process of claim 2, wherein the inorganic base is a mixture of bases and is used as a solid.

5. The process of claim 1, wherein the organic solvent is an aliphatic ether having up to 8 carbon atoms or an aromatic hydrocarbon.

6. The process of claim 5, wherein the aliphatic ether is methyl t-butyl ether or tetrahydrofuran.

7. The process of claim 5, wherein the aromatic hydrocarbon is toluene.

8. The process of claim 1, wherein the phase transfer catalyst is selected from the group consisting of quaternary ammonium compounds and phosphonium compounds.

9. The process of claim 8, wherein the phase transfer catalyst is tetrabutylammonium hydrogensulfate.

10. The process of claim 1, wherein the reacting is at a temperature from about 80° C. to reflux.

11. The process of claim 10, wherein the reacting is at a temperature of about 90° C.

* * * * *